United States Patent [19]

Dahlinder et al.

[11] Patent Number: 5,246,714
[45] Date of Patent: Sep. 21, 1993

[54] DRUG PREPARATION

[75] Inventors: Lars-Erik D. Dahlinder, Mölndal; Mats O. Johansson, Göteborg; John A. Sandberg, Mölndal; John A. Sjögren, Mölnlycke, all of Sweden

[73] Assignee: Aktiebolaget Hassle, Molndal, Sweden

[21] Appl. No.: 884,476

[22] Filed: May 13, 1992

Related U.S. Application Data

[63] Continuation of Ser. No. 476,988, Feb. 8, 1990, abandoned, which is a continuation-in-part of Ser. No. 907,599, Sep. 12, 1986, Pat. No. 4,927,640.

[30] Foreign Application Priority Data

Oct. 11, 1985 [SE] Sweden .................................. 8504720

[51] Int. Cl.$^5$ ............................................. A61K 9/16
[52] U.S. Cl. ................................. 424/497; 424/490; 424/489; 424/468; 424/464; 424/451
[58] Field of Search ............... 424/497, 490, 489, 468, 424/464, 451

[56] References Cited

U.S. PATENT DOCUMENTS 3,390,050 6/1968 Speiser ............................. 424/490

OTHER PUBLICATIONS

Connine, Preparation of Small Pharmaceutical Spheres D & CI/Apr. 1970.
Remingtons Pharmaceutical Sciences, 17th edition, 1985.

Primary Examiner—Thurman K. Page
Assistant Examiner—William E. Benston, Jr.
Attorney, Agent, or Firm—White & Case

[57] ABSTRACT

Controlled release preparation containing a number of insoluble beads applied with one or more pharmaceutically active compounds, a method for the production thereof and the use in a treatment where a controlled release of a pharmaceutically active compound is needed.

7 Claims, 3 Drawing Sheets

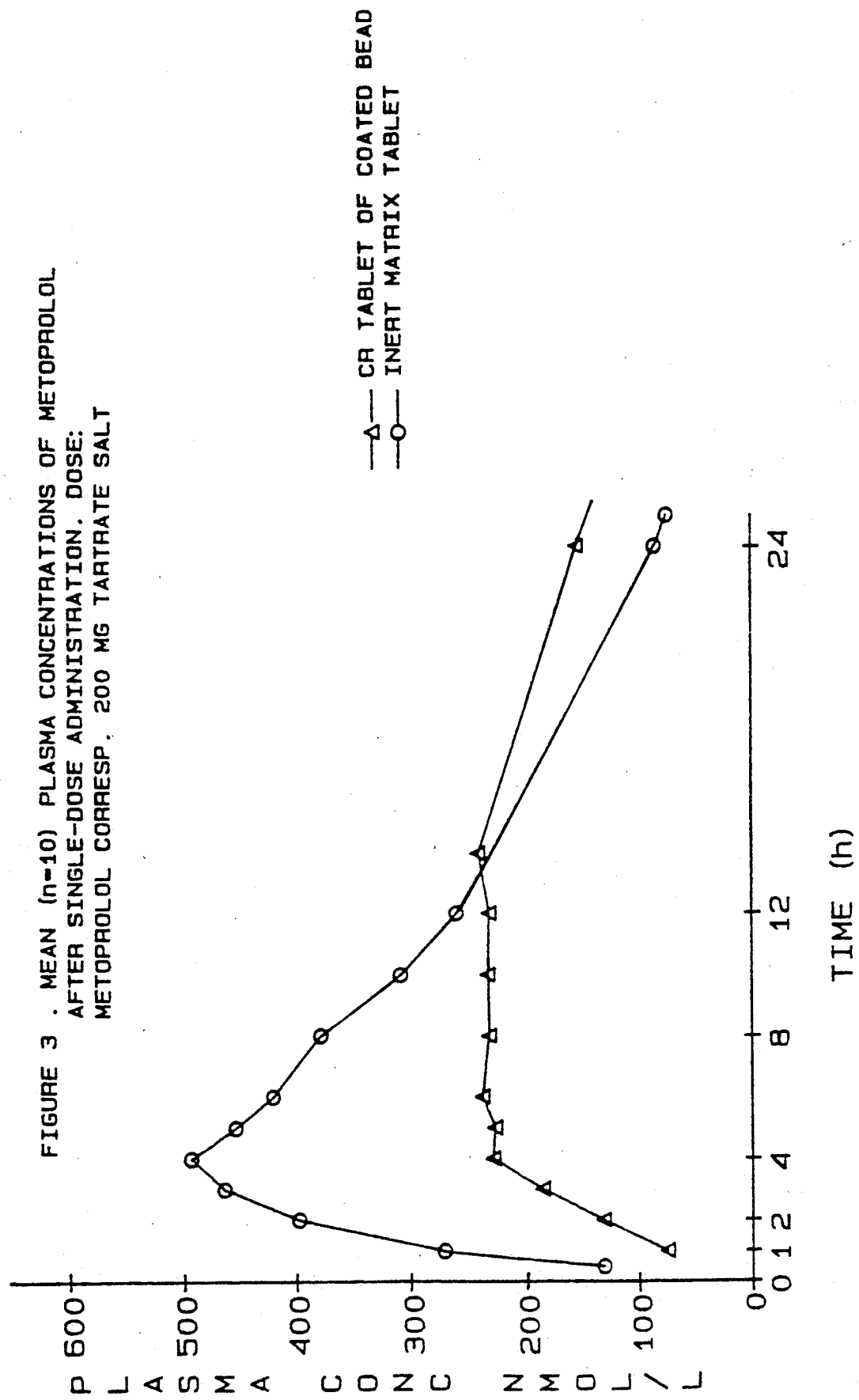

DRUG PREPARATION

This application is a continuation of application Ser. No. 07/476,988, filed on Feb. 8, 1990, abandoned which is a continuation-in-part of U.S. Ser. No. 06/907,599, filed Sep. 12, 1986 now U.S. Pat. No. 4,927,640.

FIELD OF THE INVENTION

The present invention is related to new pharmaceutical preparations with controlled release of a pharmaceutically active compound, to a method for the manufacture of such preparations and to a method of obtaining controlled release of a pharmaceutically active compound.

BACKGROUND OF THE INVENTION

In the medical treatment of various diseases, e.g. in the cardiovascular, gastrointestinal and chemotherapeutic field, it is an advantage to have a constant concentration of the administered drug in the blood. Thus a controlled release of the drug from the pharmaceutical preparation is wanted.

It is important that the controlled release preparation delivers the amount of drug needed to maintain an adequate and even effect during the entire therapeutic dosage interval. This usually means that the drug should be delivered at a constant rate to give an even concentration of the administered drug in the blood which is of specific importance for drugs having a small therapeutic index, i.e. a small difference between effective and toxic concentration. A delayed and constant release of the drug will also be of importance for locally irritating drugs having a potential risk of causing gastrointestinal disturbances when present in large local concentrations or for drugs having a short elimination half-life. In the latter case less frequent administration and thus better patient compliance (cf. Hayes R. B. et al. Clin. Pharm. Therap. (1977), 22, pp. 125–130) may be obtained with controlled release preparations compared with conventional dosage forms.

A drug can be delivered in a controlled way via any route of administration but the preparations should preferably have some features in common, e.g. give a controlled and reproducible release of drug and contribute to a reproducible absorption, have no toxic or irritating constituents and be suitable also for high dosage drugs.

Examples of drug delivery systems for oral use with a controlled release of the drug are e.g. sustained release tablets of the insoluble matrix type, such as Durules®, and the osmotically active tablet, OROS®. The OROS® system is described in U.S. Pat. No. 4,036,227 and in a supplement to British Journal of Clinical Pharmacology (1985), 19, 695–765 by Theeuwes F. et al. It consists of a tablet core of the drug substance as the major constituent which is surrounded with a semipermeable polymeric membrane through which a small opening is drilled. DE-A-2030501 describes a preparation of the matrix type which contains amorphous silicon dioxide. The active compound is released by diffusion through the matrix. The examples above are single-unit systems with all drug substance concentrated in one unit while the present invention is of the multiple-unit principle.

From GB-A-1542414 a composition is known containing an organic support material to which an active compound is physically or chemically bound and a glass material in contact with said support material. The glass contains soluble metal ions. The release of drug is governed by the dissolution of metal ions from the glass material due to an ion exchange process. Obviously, the glass is not an insoluble inert compound of the composition.

Several advantages with depot preparations comprising a large number of small units have been described in the literature. It is, for example, possible to obtain a reproducible emptying of the units from the stomach into the small intestine when the particles are less than 1–2 mm (cf. Bogentoft C. et al: Influence of food on the absorption of acetylsalicylic acid from enteric coated dosage forms. Europ. J. Clin. Pharmacol. (1978), 14, 351–355). Dispersion over a large area in the gastrointestinal canal can give a more reproducible total time for the passage, which is of advantage for the absorption process (cf. Edgar B. et al: Comparison of two enteric-coated acetylsalicylic acid preparations by monotoring steady-state levels of salicylic acid and its metabolites in plasma and urine. Biopharmaceutics & Drug Disposition, (1984), 5, 251–260). In addition a multiple unit preparation is preferable to one single drug unit as the dose is spread out in the intestine. The risk of local irritation and accumulation of several doses due to constriction in the alimentary canal are also considered to be lower, (cf. McMahan F. G. et al: Upper gastrointestinal lesions after potassium chloride supplements: A controlled clinical trial The Lancet, Nov. 13, 1059–1061).

A further advantage with a multiple unit preparation is that it may be divided into smaller portions all having the same absorption properties. This makes it possible to obtain a greater flexibility in selecting the size of the dose.

BRIEF DESCRIPTION OF THE DRAWING

FIG. 3 represents the plasma concentration of metoprolol over a period of time.

OUTLINE OF THE INVENTION

Figure 1:
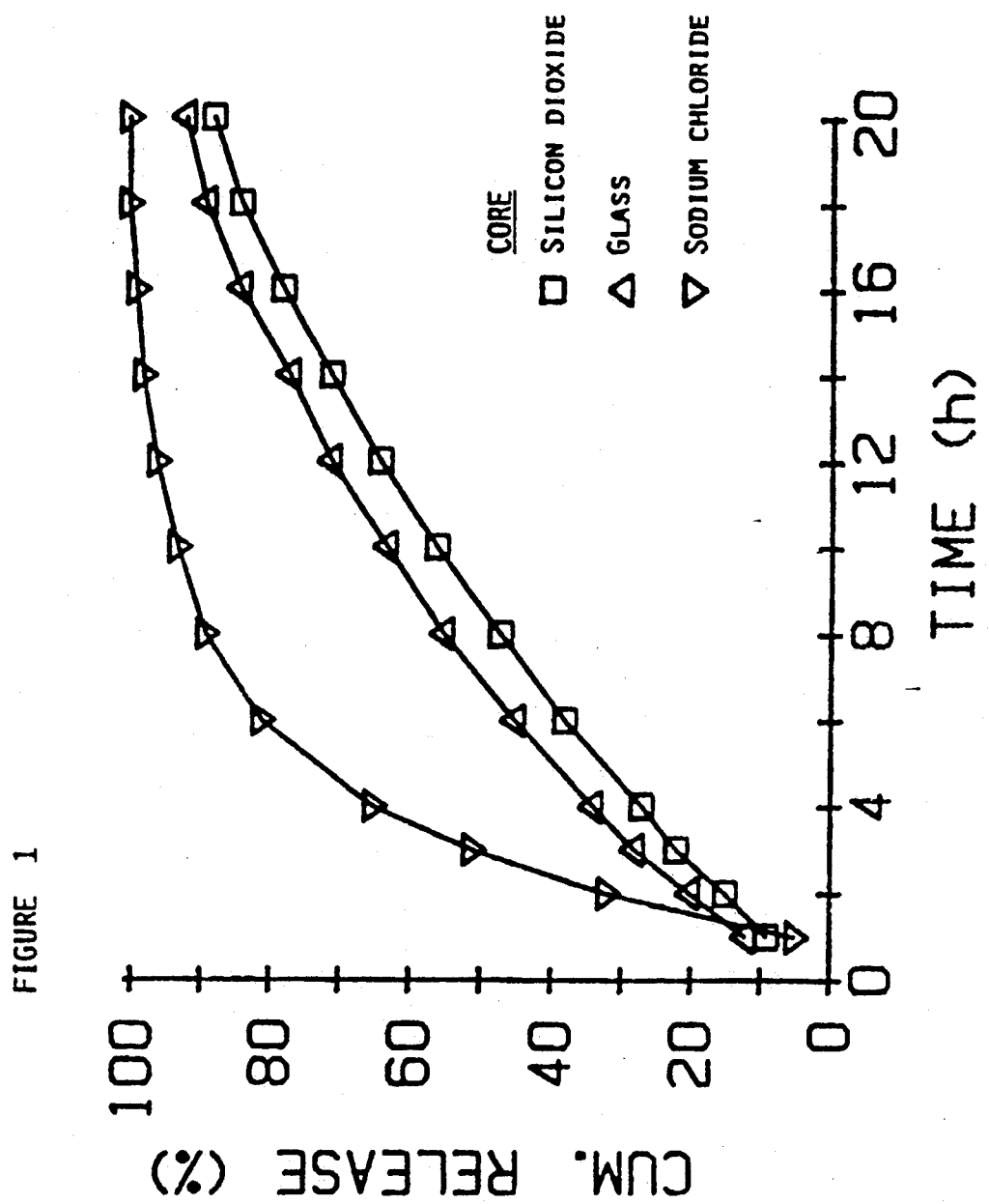
FIG. 1 represents the cumulative release, expressed in percents over a period of time, expressed in hours, from core of silicon dioxide, glass and sodium chloride.

The present invention is related to a new type of preparation giving a controlled release of one or more pharmaceutically active compounds.

The preparation consists of a large number of small insoluble particles, cores, which are covered by a pharmaceutically active compound. The cores have a size of 0.1–2 mm, preferably 0.1–0.5 mm, and consist of insoluble inert material. Insoluble means that the material is not soluble in water, physiological fluids or in common liquids used for intravenous infusion. Examples of insoluble inert material are silicon dioxide, glass, or plastic resin particles. Suitable types of plastic materials are pharmaceutically acceptable plastics, such as polypropylene or polyethylene, preferably polypropylene. The core material should have a standardized size and shape, preferably spherical with an even surface. Preferably, the core material should have a sufficiently high density which makes it suitable for a fluidized-bed process. Furthermore, it is important that the core material has a high degree of purity, that is, is free from soluble contaminating compounds.

The pharmaceutically active compound is applied on the core material preferably by spraying from a solution. The active compound thereby forms a compact layer on the insoluble core. Pharmaceutically active compounds used are such having cardiovascular, gastrointestinal or chemotherapeutic effect, especially adreneric beta-blocking agents and antibiotics. Examples of suitable pharmaceutically active compounds which can be applied on the core material are salts of alprenolol, metoprolol, quinidine, magnesium, and ampicillin. The resulting particles or beads have a size of 0.2-3.0 mm, preferably 0.3-1.0 mm. It is however possible to form controlled release preparations according to the method above for most drugs for which such preparations are wanted, provided they can be dissolved in a solvent that can be dried off during processing.

The beads according to the invention are compact, which means that the porosity is less than 15 percent.

The beads are coated with a polymeric membrane modifying and controlling the drug release. The polymeric membrane can release the drug according to various release profiles, e.g. pH dependent, enteric coating, pH independent, with or without lag time. The most important use is pH independent controlled release in the range of pH 1-8. Examples of suitable polymeric materials are ethyl cellulose, hydroxypropylmethyl cellulose, hydroxypropyl cellulose, hydroxypropylmethyl phthalate (e.g. HP 55), cellulose acetate phthalate, Eudragit ®RL, Eudragit ®RS. Ethyl cellulose can be used alone or in a combination with e.g. a water soluble polymer such as hydroxypropylmethyl cellulose to adjust the permeability of the coating layer.

Ethyl cellulose is available in grades having different viscosities. In the examples given below, ethyl cellulose qualities with a viscosity of 10, 50 or 100 cps are used, but also other types of ethyl cellulose are suitable.

Eudragit ® is the trade name for a number of film coating substances on an acrylic resin basis produced by Röhm Pharma. E.g. Eudragit RL and RS are copolymers synthetized from acrylic and methacrylic acid esters with a low content of quaternary ammonium groups. The molar ratio of these ammonium groups to the remaining neutral (meth)acrylic acid esters is 1:20 for Eudragit ®RL and 1:40 for Eudragit ®RS resulting in different permeability characteristics. Other variants of Eudragit that can be used are Eudragit L, Eudragit S and Eudragit E.

Pigments and/or plasticizers may be added to the polymeric solution in order to improve the technical properties of the membrane or modify the release characteristics. Examples of plasticizers that may be used are citrate esters, acetylated monoglycerides, and glycerinetriacetate.

The new preparation has several advantages, e.g. the particles contain a high percentage of active ingredient and are not contaminated by soluble inert compounds, which is the case, when cores of e.g. lactose or sugar are covered by a therapeutically active compound. This is especially important when the preparation is used for parenteral administration.

By using small dense particles of e.g. silicon dioxide as the core material, it is possible to obtain highly concentrated beads (granules) of the active compound which is an advantage for high dosage preparations, e.g. magnesium chloride.

An advantage with the new preparation is that in general less polymeric material is needed to obtain a delayed drug release when the insoluble cores applied with an active compound are coated compared to when preparations having a soluble core material are coated (cf. FIG. 1). The preparation according to the invention can be administered by various routes, e.g. orally or parenterally. An example of intravenous administration is via the drug-administration-device described in EP-B1-59694.

When using the coated beads of active compound according to this invention for oral application, it is possible to formulate the preparation as granules filled into hard gelatine capsules, filled into sachets or formed into tablets and still obtain the desired plasma concentration profile and duration of the effect after administration.

When the small beads are tabletted they are mixed with additives containing e.g. microcrystalline cellulose, such as Avicel ®, which improves the tabletting properties and facilitates the disintegration of the tablet to liberate the individual beads.

The invention makes it possible to obtain a decreased dosing frequency and still have an almost constant concentration of the drug in the plasma during the whole period until the next dose is administered. A single dose a day is often sufficient with the new preparation.

A process for the manufacture of a controlled release preparation represents a further aspect of the invention. The pharmaceutically active compound is dissolved in a suitable solvent e.g. methylene chloride, ethanol, isopropylic alcohol or water and sprayed onto the insoluble core material in a coating pan or preferably in a fluidized bed and the solvent is dried off. The beads obtained are then coated with a polymeric layer described above. The polymeric mixture is dissolved in a solvent such as ethanol, isopropyl alcohol and/or methylene chloride. The spraying can be carried out in a coating pan, but is preferably carried out in a fluidized bed. Ethyl cellulose can also be applied from an aqueous dispersion (latex).

The preparation according to the invention is particularly advantageous when a controlled and constant release of a therapeutically active compound is wanted. A method for the controlled release of therapeutically active compounds represents a further aspect of the invention.

The invention is described in detail in the following examples:

EXAMPLES

Example 1

| Cores | |
|---|---|
| Metoprolol fumarate | 1440 g |
| Methylene chloride | 9618 g |
| Ethanol 95% | 3888 g |
| SiO$_2$ (0.15–0.25 mm) | 375 g |

| Polymeric layer | |
|---|---|
| Ethyl cellulose 10 cps | 265.6 g |
| Hydroxypropylmethyl cellulose | 58.4 g |
| Acetyltributylcitrate | 36.0 g |
| Methylene chloride | 6141 g |
| Isopropylic alcohol | 1544 g |

In a fluidized bed granulator metoprolol fumarate was sprayed onto the cores of silicon dioxide from a solution of ethanol 95%. 400 g of the beads so formed (fraction 0.4–0.63 mm) were covered with the polymeric solution containing ethyl cellulose 10 cps, hydroxypropylmethyl cellulose and acetyltributylcitrate by spraying a solution of the mentioned substances in methylene chloride and isopropylic alcohol. The coated beads were then filled into hard gelatine capsules.

Examples 2-3 and Reference 1

| Cores | 2 | 3 | Reference 1 |
|---|---|---|---|
| Metoprolol succinate | 1440 g | 1440 g | 1440 g |
| Methylene chloride | 9618 g | 9618 g | 9618 g |
| Ethanol 95% | 3888 g | 3888 g | 3888 g |
| SiO₂ (0.15–0.25 mm) | 375 g | | |
| Glass (0.2 mm) | | 375 g | |
| NaCl (0.15–0.25 mm) | | | 375 g |

Polymer layer 400 g of the granules (fraction 0.4–0.5 mm) above were coated with a composition comprising

| Ethyl cellulose 10 cps | 52.3 g |
|---|---|
| Acetyltributylcitrate | 8.6 g |
| Methylene chloride | 1111 g |
| Isopropylic alcohol | 218 g |

Figure 2:
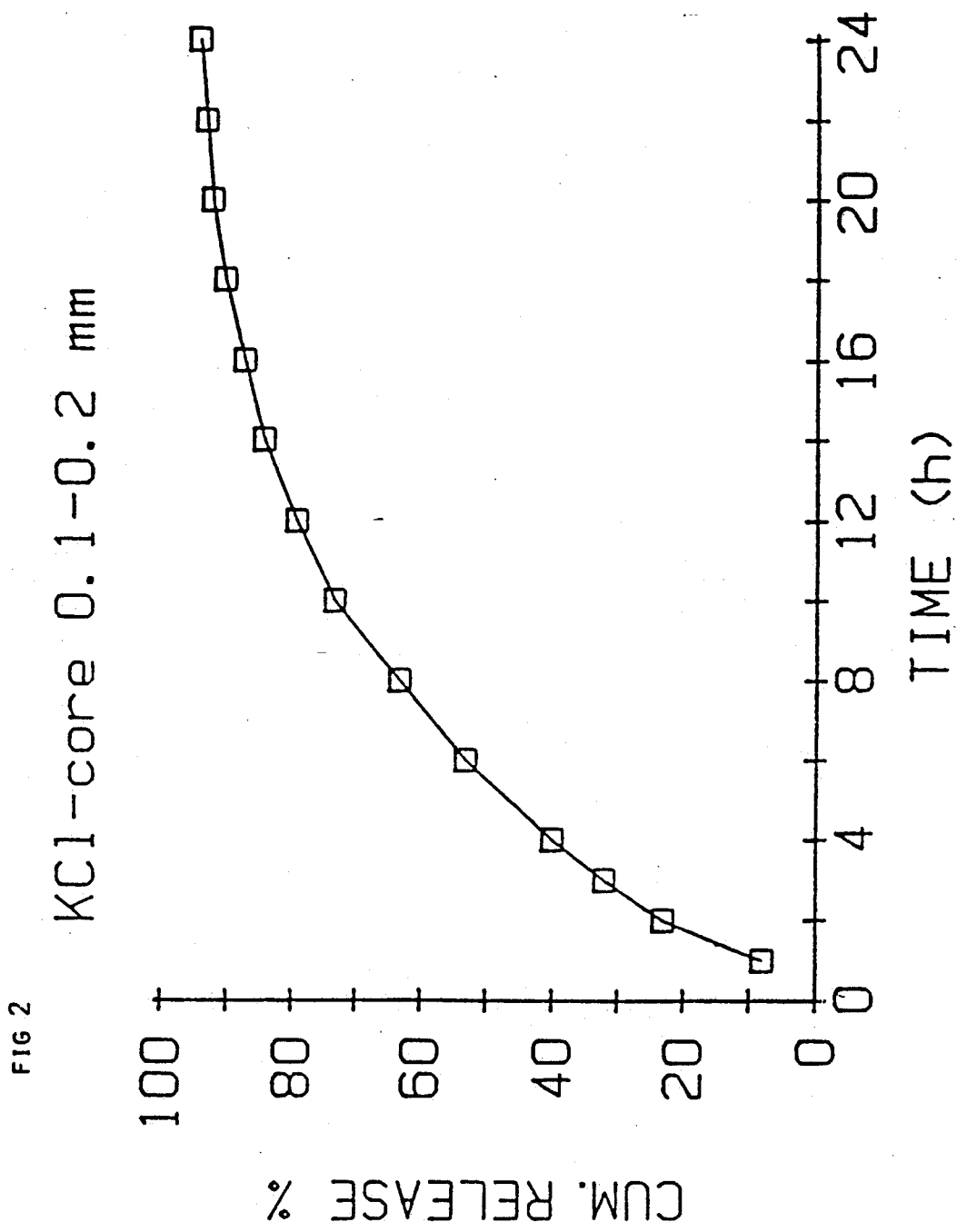
FIG. 2 represents the cumulative release expressed in percents, over a period of time, expressed in hours, from a potassium chloride core.

Metoprolol succinate was sprayed onto the cores of silicon dioxide, glass and sodium chloride, respectively, from a solution of ethanol 95% and methylene chloride. The beads so formed were coated with the polymeric solution containing ethyl cellulose 10 cps and acetyltributylcitrate dissolved in methylene chloride and isopropylic alcohol by spraying. FIG. 1 illustrates the cumulative release of metoprolol succinate during 20 hours. As can be seen from the figure a controlled and almost constant release of the active compound was obtained, when the active compound was applied on silicon dioxide or glass, whereas a core of soluble sodium chloride resulted in a considerably higher initial release rate, which also is illustrated in FIG. 2 (Reference 2 below) where soluble potassium chloride was used as core material.

Reference 2

| Cores | |
|---|---|
| Metoprolol succinate | 2000 g |
| KCl (0.1–0.2 mm) | 400 g |
| Methylene chloride | 13360 g |
| Ethanol 95% | 7900 g |

400 g of the granules according to Reference 2 were coated with a composition comprising

| Polymeric layer | |
|---|---|
| Ethyl cellulose 10 cps | 135.3 g |
| Eudragit ® RS | 27.4 g |
| Acetyltributylcitrate | 27.4 g |
| Methylene chloride | 4469 g |
| Isopropylic alcohol | 661 g |

The granules were formulated as described in the previous examples.

EXAMPLES 4–6

| Cores | Example | | |
|---|---|---|---|
| | 4 | 5 | 6 |
| Metoprolol succinate | 1440 g | 1440 g | 1440 g |
| Methylene chloride | 9618 g | 9618 g | 9618 g |
| Ethanol 95% | 3888 g | 3888 g | 3888 g |
| SiO₂ (0.15–0.2 mm) | 375 g | | |
| SiO₂ (0.25–0.3 mm) | | 375 g | |
| SiO₂ (0.4–0.5 mm) | | | 375 g |

400 g of the granules according to Examples 4–6 were coated with a composition comprising

| Polymeric layer | granulate according to Example | | |
|---|---|---|---|
| | 4 | 5 | 6 |
| Ethyl cellulose 10 cps | 187.2 g | 144.0 g | 92.2 g |
| Hydroxypropylmethyl cellulose | 46.8 g | 36.0 g | 23.0 g |
| Acetyltributylcitrate | 26.0 g | 20.0 g | 12.8 g |
| Methylene chloride | 4428 g | 3408 g | 2168 g |
| Isopropylic alcohol | 1114 g | 858 g | 546 g |

The preparations were formulated as described above. In the enclosed Table 1 the release of metoprolol succinate during 20 hours is given. All preparations gave a controlled release of drug during a long period of time.

Example 7

| Cores | |
|---|---|
| Magnesium chloride, hexahydrate | 1100 g |
| Ethanol 99.5% | 6200 g |
| Silicon dioxide (0.15–0.30 mm) | 400 g |

| Polymeric layer | |
|---|---|
| Ethyl cellulose 50 cps | 533 g |
| Methylene chloride | 14107 g |
| Isopropylic alcohol | 5481 g |

Magnesium chloride (MgCl₂) was sprayed onto the cores of silicon dioxide from a solution of ethanol 99.5%. 400 g of the beads so formed were coated with ethyl cellulose 50 cps from a solution of methylene chloride and isopropylic alcohol to give granules containing 347 mg/g magnesium chloride (MgCl₂). The in vitro release of drug was 38% after 1 hour, 58% after 2 hours and 82% after 6 hours.

EXAMPLE 8

| Cores | |
|---|---|
| Ampicillin - Na | 600 g |
| Ethanol 95% | 894 g |
| Water purified | 1020 g |
| Glass (0.5 mm) | 500 g |

| Polymeric layer | |
|---|---|
| Ethyl cellulose 100 cps | 15 g |
| Methylene chloride | 600 g |

| Polymeric layer | |
|---|---|
| Isopropylic alcohol | 150 g |

Ampicillin-Na was sprayed onto the cores of glass from the ethanol/water solution. 500 g of the ampicillin-Na beads were then coated with a polymeric solution of ethyl cellulose 100 cps in methylene chloride/isopropylic alcohol. After 40 minutes in vitro dissolution 50% of the drug content was released from the beads.

EXAMPLE 9

| Cores | |
|---|---|
| Metoprolol succinate | 1440 g |
| Methylene chloride | 9618 g |
| Ethanol 95% | 3888 g |
| SiO$_2$ (0.15–0.25 mm) | 375 g |

| Polymeric layer | |
|---|---|
| Ethyl cellulose N-10 | 166.2 g |
| Hydroxypropylmethyl cellulose | 39.0 g |
| Acetyltributylcitrate | 22.8 g |
| Methylene chloride | 3889 g |
| Isopropylic alcohol | 978 g |

| Tablet additives | |
|---|---|
| Microcrystalline cellulose | 429.3 g |
| Corn starch | 67.1 g |
| Lactose powder | 40.3 g |
| Polyvidone | 55.5 g |
| Water purified | 314.7 g |
| Magnesium stearate | 1.2 g |

| Tablet coating (12.500 tablets) | |
|---|---|
| Hydroxypropylmethyl cellulose 6 cps | 159.6 g |
| Polyethylene glycol 6000 | 39.9 g |
| Colour Titanium Dioxide | 39.9 g |
| Water purified | 1356 g |
| Paraffin | 1.6 g |

Metoprolol succinate was sprayed onto the cores of silicon dioxide according to the process described in the previous examples. 400 g of the so obtained beads (fraction 0.4–0.63 mm) were coated with the polymeric solution described above. The coated beads of metoprolol succinate were mixed with the additives in equal portions and after addition of Mg-stearate 0.1%, the dry mixture was compressed to tablets. Finally, the tablets were coated in a coating pan with the polymeric solution described above.

The very small particles, 0.15–0.25 mm, of dense SiO$_2$ used as the core material, contribute to a high content of drug in the small beads formed (0.4–0.63 mm) and thus to a reduced size of the final preparation.

EXAMPLE 10

| Cores | |
|---|---|
| Omeprazole-Sodium | 90 g |
| Purified water | 180 g |
| Polypropylene (1.25–1.60 mm) | 450 g |

| Polymeric Layer | |
|---|---|
| Ethylcellulose N 50 | 50 g |
| Ethanol 99.5% | 1617 g |

The manufacture was carried out in one process step using a fluidized bed apparatus with bottom spray equipment (Wurster). Omeprazole-Sodium was sprayed onto the plastic cores of polypropylene from a 33% water solution of the drug. The drug particles so formed were subsequently coated with the polymeric solution of ethylcellulose in ethanol. Total yield was 88.6%.

The coated drug beads were sieved to discharge agglomerates. The beads were analysed and were found to contain 131.1 mg Omeprazole-Sodium per gram. The in vitro release of drug in a physiological sodium chloride (0.9%) solution at 25° C. was 18% after 1 hour, 41% after 6 hours and 60% after 14 hours. Method: USP dissolution apparatus No. I (rotating basket) at 100 rpm.

EXAMPLE 11

| Cores | |
|---|---|
| Omeprazole-Sodium | 19.5 g |
| Purified water | 39 g |
| Polymethylmethacrylate (0.425–0.71 mm) | 100 g |

| Polymeric Layer | |
|---|---|
| Ethylcellulose N 50 | 20 g |
| Ethanol 99.5% | 1980 g |

The same equipment and manufacturing procedures were used as in Example 10. Samples were discharged from the coating process after applying 5, 10 and 15 g of ethylcellulose. Total yield was 87.6%. The content of Omeprazole-Sodium was 69.2 mg/g beads.

In vitro release results showed that the controlled release of drug is highly dependent on the amount of film coat applied on the beads. For example, after 6 hours, 98%, 76% and 61% were released from the beads being coated with 5, 10 and 5 g of ethylcellulose, respectively. The same dissolution method was used as in Example 10.

Table 1 summarizes the drug release data for the compositions according to examples 1–6 and 9 and Reference examples 1 and 2.

The best mode of carrying out the invention is at present considered to be Examples 10–11.

TABLE 1

Cumulative in vitro release of metoprolol in a phosphate buffer pH 6.8
Method: USP apparatus No II, rotating paddle at 100 rpm

| Example No. | FIG. No. | Core material | Conc. metoprolol in the beads mg/g | 1 | 2 | 3 | 4 | 6 | 8 | 10 | 12 | 14 | 16 | 18 | 20 |
|---|---|---|---|---|---|---|---|---|---|---|---|---|---|---|---|
| 1 | | SiO$_2$ | 434 | 1 | 2 | 5 | 11 | 25 | 39 | 52 | 62 | 69 | 74 | 78 | 81 |
| 2 | 1 | SiO$_2$ | 703 | 9 | 15 | 22 | 27 | 38 | 47 | 56 | 64 | 71 | 78 | 84 | 88 |
| 3 | 1 | glass | 688 | 12 | 20 | 28 | 34 | 45 | 55 | 63 | 71 | 77 | 84 | 89 | 92 |
| Ref. 1 | 1 | NaCl | 686 | 5 | 32 | 51 | 65 | 81 | 89 | 93 | 96 | 98 | 99 | 100 | 100 |
| Ref. 2 | 2 | KCl | 619 | 8 | 23 | 32 | 40 | 53 | 63 | 73 | 79 | 84 | 87 | 90 | 92 |
| 4 | | SiO$_2$ | 513 | 1 | 2 | 3 | 8 | 21 | 34 | 48 | 61 | 72 | 80 | 84 | 88 |
| 5 | | SiO$_2$ | 565 | 1 | 2 | 4 | 8 | 19 | 29 | 40 | 51 | 62 | 71 | 78 | 83 |
| 6 | | SiO$_2$ | 620 | 4 | 8 | 12 | 17 | 28 | 37 | 46 | 54 | 62 | 68 | 74 | 79 |
| 9 | 3 | SiO$_2$ | 533 | 7 | 13 | 18 | 23 | 33 | 43 | 52 | 61 | 69 | 76 | 82 | 86 |

We claim:

1. Controlled release beads, each comprising a compact inert core consisting of a plastic resin selected from the group consisting of polypropylene and polyethylene; an active layer applied to the surface of the insoluble core consisting essentially of one or more pharmaceutically active compounds; and a release controlling polymeric membrane covering the active layer.

2. Beads according to claim 1 wherein the core has a size of 0.1–2 mm and the combination of the core and the layer has a size of 0.2–3.0 mm.

3. Beads according to claim 2, wherein the core has a size of 0.1–0.5 mm and the combination of the core and the active layer has a size of 0.3–1.0 mm.

4. Beads according to claim 1 wherein the pharmaceutically active compound is to be administered orally or parenterally.

5. Beads according to claim 1 wherein the pharmaceutically active compound is used in the cardiovascular, gastrointestinal or chemotherapeutic field.

6. Beads according to claim 1 wherein the pharmaceutically active compound is selected from the group consisting of a salt of an adrenergic beta-blocking agent, an antibiotic and a gastric acid secretion inhibitor.

7. A process for the preparation of beads for use in controlled release products consisting essentially of
   (a) dissolving a pharmaceutically active compound in a solvent;
   (b) applying the dissolved active compound to an insoluble core consisting of a plastic resin selected from the group consisting of polypropylene and polyethylene having a size of 0.2 to 2.00 mm;
   (c) drying the insoluble core to remove the solvent and form beads having a coating of active compound and a size of 0.2 to 3.0 mm; and
   (d) further coating the beads with a release controlling polymeric membrane.

* * * * *